(12) United States Patent
Rekhter

(10) Patent No.: US 10,112,951 B2
(45) Date of Patent: Oct. 30, 2018

(54) PDE1 INHIBITOR

(71) Applicant: Eli Lilly and Company, Indianapolis, IN (US)

(72) Inventor: Mark David Rekhter, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/834,256

(22) Filed: Dec. 7, 2017

(65) Prior Publication Data

US 2018/0099973 A1    Apr. 12, 2018

Related U.S. Application Data

(62) Division of application No. 15/423,626, filed on Feb. 3, 2017, now Pat. No. 9,868,741.

(60) Provisional application No. 62/294,329, filed on Feb. 12, 2016.

(51) Int. Cl.
*C07D 487/04* (2006.01)
*A61K 31/4985* (2006.01)

(52) U.S. Cl.
CPC ........ *C07D 487/04* (2013.01); *A61K 31/4985* (2013.01)

(58) Field of Classification Search
CPC .......................... A61K 31/4958; C07D 487/04
See application file for complete search history.

(56) References Cited

U.S. PATENT DOCUMENTS

| | | | |
|---|---|---|---|
| 6,451,796 B1 | 9/2002 | Kobayashi et al. |
| 8,299,080 B2 | 10/2012 | Okada et al. |
| 9,175,010 B2 | 11/2015 | Branstetter et al. |

FOREIGN PATENT DOCUMENTS

| | | | |
|---|---|---|---|
| CA | 2345752 A1 * | 6/2000 | ............ A61K 31/00 |
| EP | 0 040 401 B1 | 5/1981 | |
| EP | 2103613 A1 | 9/2009 | |
| EP | 2615096 A1 | 7/2013 | |
| WO | 2008103357 A1 | 8/2008 | |

OTHER PUBLICATIONS

Brown et al (Year: 2014).*
Al-Salahi, Rashad "Synthesis of Novel 2-Alkoxy(aralkoxy)-4H-[1,2,4]triazolo[1,5-a]quinazolin-5-ones Starting with Dialkyl-N-Cyanoimidocarbonates", Journal of Heterocyclic Chemistry, 2011, vol. 48, pp. 656.
U.S. Appl. No. 15/680,250 pending in the USPTO, filed Aug. 18, 2017; Eli Lilly and Company.
Chen et al.(J. Mol. Hist., 2013, 44, 693-703).

* cited by examiner

*Primary Examiner* — Rachael E Bredefeld
*Assistant Examiner* — Ibrahim D Bori
(74) *Attorney, Agent, or Firm* — Nelsen L Lentz

(57) ABSTRACT

The present invention provides a compound of Formula I:

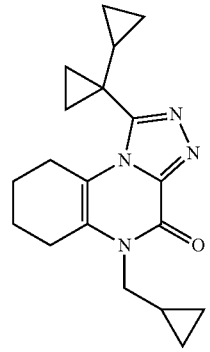

Formula I useful for treating chronic kidney disease and diabetic kidney disease.

2 Claims, No Drawings

PDE1 INHIBITOR

The present invention relates to a certain PDE1 inhibitor, to pharmaceutical compositions comprising the compound, to methods of using the compound to treat physiological disorders, and to intermediates and processes useful in the synthesis of the compound.

Phosphodiesterases (PDEs) are enzymes that regulate the cellular levels of cAMP and cGMP by controlling the rate at which these cyclic nucleotides are hydrolyzed. PDE1, a calcium and calmodulin-dependent PDE, is one of at least 11 known PDE families. PDE1 is expressed in many tissues, including the brain, heart, lung, kidney, and smooth muscle. In addition, PDE1 is comprised of a family of three known isoforms, PDE1A, PDE1B, and PDE1C.

Patients suffering from diabetes often develop a form of chronic kidney disease referred to as diabetic kidney disease (or diabetic nephropathy). It has been estimated that diabetic kidney disease may affect as many as 40 percent of diabetic patients. Treatment options for diabetic kidney disease is limited and includes use of medications that lower blood pressure, management of blood glucose levels, diet, and weight, and implementation of regular physical activity. Thus, there is a need for additional treatment choices for patients suffering from chronic kidney disease, particularly diabetic kidney disease.

U.S. Pat. No. 9,175,010 discloses certain thiophene-, furan-, and pyridine-fused azolopyrimidin-5-(6H)-ones which are inhibitors of PDE1, and more particularly, PDE1B, as being useful for treating various physiological disorders, including neurological, cardiovascular, and renal disorders. In addition, European Patent No. 0 040 401 discloses certain substituted triazoloquinoxalin-4-ones possessing anti-hypertensive activity.

The present invention provides a certain novel compound that is an inhibitor of PDE1. In addition, the present invention provides a certain novel compound that is a selective inhibitor of PDE1B relative to other PDEs, such as PDE2A, PDE3A, PDE4D, PDE5A, PDE6AB, PDE7B, PDE8A, PDE9A, PDE10A, and PDE11A. Furthermore, the present invention provides a certain novel compound that may have antihypertensive effects and may also improve renal blood flow. In addition, the compound of the present invention may reduce renal fibrosis.

Accordingly, the present invention provides a compound of Formula I:

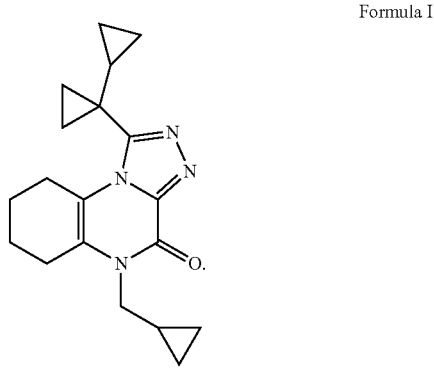 [SMILES: O=c1c2nnc(C3(C4CC4)CC3)n2c2c(n1CC1CC1)CCCC2]

Formula I

The present invention also provides a method of treating chronic kidney disease in a patient, comprising administering to a patient in need of such treatment an effective amount of a compound of Formula I.

The present invention also provides a method of treating diabetic kidney disease in a patient, comprising administering to a patient in need of such treatment an effective amount of a compound of Formula I.

The present invention also provides a method of treating hypertension in a patient, comprising administering to a patient in need of such treatment an effective amount of a compound of Formula I.

In addition, the invention provides a compound of Formula I for use in therapy. The invention further provides a compound of Formula I for use in for the treatment of chronic kidney disease. In addition, the invention provides a compound of Formula I for use in the treatment of diabetic kidney disease. In addition, the invention provides a compound of Formula I for use in the treatment of hypertension. Furthermore, the invention provides the use of a compound of Formula I for the manufacture of a medicament for the treatment of chronic kidney disease. Furthermore, the invention provides the use of a compound of Formula I for the manufacture of a medicament for the treatment of diabetic kidney disease. The invention further provides the use of a compound of Formula I for the manufacture of a medicament for the treatment of hypertension.

The invention further provides a pharmaceutical composition, comprising a compound of Formula I with one or more pharmaceutically acceptable carriers, diluents, or excipients. The invention further provides a process for preparing a pharmaceutical composition, comprising admixing a compound of Formula I with one or more pharmaceutically acceptable carriers, diluents, or excipients. This invention also encompasses novel intermediates and processes for the synthesis of the compound of Formula I.

As used herein, the terms "treating", "treatment", or "to treat" includes prohibiting, restraining, slowing, stopping, or reversing the progression or severity of an existing symptom or disorder.

As used herein, the term "patient" refers to a mammal, such as a mouse, guinea pig, rat, dog, or human. It is understood that the preferred patient is a human.

As used herein, the term "effective amount" refers to the amount or dose of compound of the invention, which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compound of Formula I is generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the invention are preferably formulated as pharmaceutical compositions administered by any route which makes the compound bioavailable, including oral and parenteral routes. Most preferably, such compositions are for oral administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

Certain abbreviations are defined as follows: "ACN" refers to acetonitrile; "AcOH" refers to glacial acetic acid; "DBU" refers to 1,8-diazabicyclo[5.4.0]undec-7-ene; "DCE" refers to 1,2-dichloroethane; "DCM" refers to dichloromethane or methylene chloride; "DIPEA" refers to N,N-diisopropylethylamine; "DMF" refers to N,N-dimethylformamide; "DMSO" refers to dimethylsulfoxide; "EDCI" refers to 1-ethyl-3-(3-dimethylaminopropyl)carbodiimide; "EtOAc" refers to ethyl acetate; "Et$_2$O" refers to diethyl ether; "EtOH" refers to ethanol; "HATU" refers to N-[(dimethylamino)-1H-1,2,3-triazolo-[4,5-b]pyridin-1-yl-methylene]-N-methylmethanaminium hexafluorophosphate N-oxide; "HMDS" refers to hezamethyldisilazane; "HOAT" refers to 1-hydroxy-7-azabenzotriazole; "HOBt" refers to hydroxybenzotriazole; "hr" refers to hour or hours; "IC$_{50}$" refers to the concentration of an agent that produces 50% of the maximal inhibitory response possible for that agent; "LC-ES/MS" refers to Liquid Chromatography Electrospray Mass Spectrometry; "LHMDS" refers to lithium bis(trimethylsilyl)amide; "µmol" refers to micromole or micromoles; "min" refers to minute or minutes; "MeOH" refers to methanol or methyl alcohol; "MTBE" refers to methyl-tert-butyl ether; "NiNTA" refers to chromatography with an agarose stationary phase functionalized with nitrilotriacetic acid as chelator; "POCl3" refers to phosphorus oxychloride; "RT" refers to room temperature; "TEA" refers to triethylamine; "TMA" refers to trimethylamine; "TFA" refers to trifluoroacetic acid; "TFAA" refers to trifluoroacetic anhydride; "THF" refers to tetrahydrofuran; "U/ml" refers to units per milliliter.

The compounds of the present invention may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention.

Scheme 1

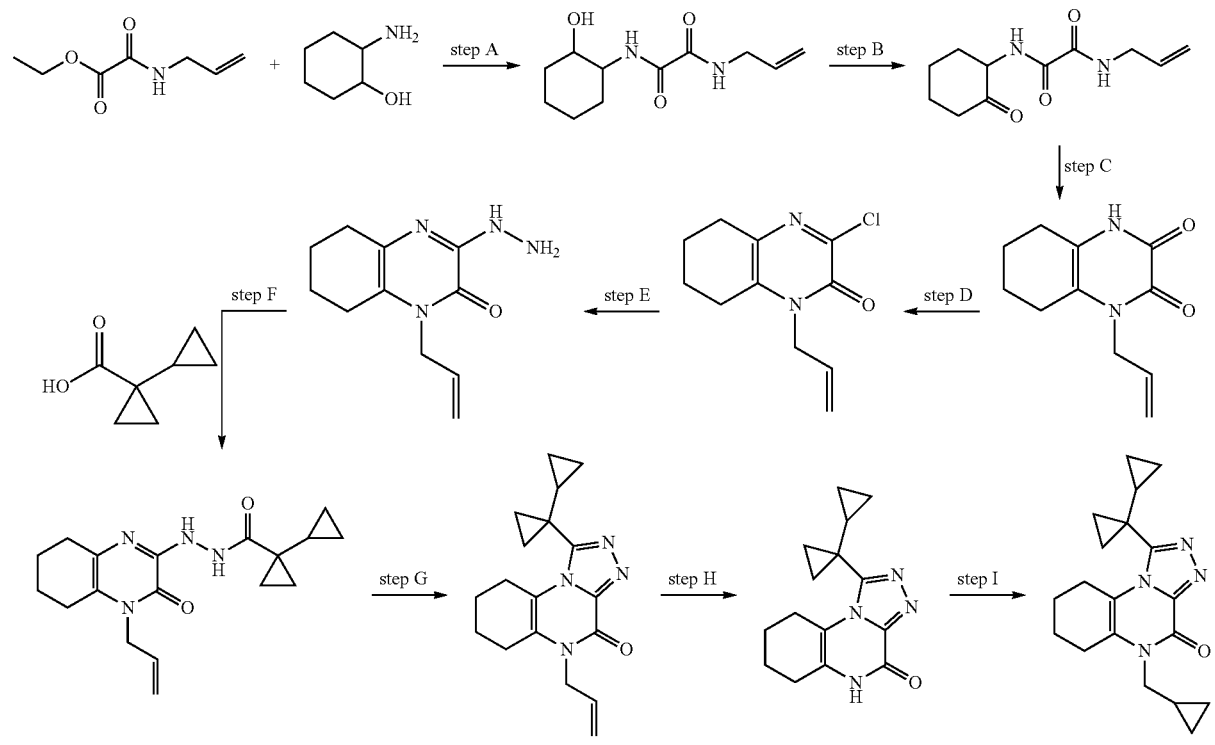

Formula I

Scheme 1 depicts the synthesis of the compound of Formula I. In Scheme 1, step A, about 1 equivalent of ethyl-2-(allylamino)-2-oxo-acetate is condensed with about 1.05 equivalents of 2-aminocyclohexanol in the presence of about 1.1 equivalents of a suitable non-nucleophilic organic base such as TEA in a polar organic solvent such as EtOAc with heating. The product may be isolated utilizing standard techniques well known in the art, such as filtration. For example, the reaction mixture is cooled and the resulting precipitate is collected by filtration, with subsequent washing with a suitable organic solvent such as EtOAc or Et₂O and drying under vacuum to provide N-allyl-N'-(2-hydroxycyclohexyl)oxamide, the product of Scheme 1, step A, as a mixture of cis and trans isomers of sufficient purity for subsequent use without additional purification.

In Scheme 1, step B, N-allyl-N'-(2-hydroxycyclohexyl) oxamide, the product of Scheme 1, step A, may be oxidized under conditions well known in the art. For example, about 1 equivalent of N-allyl-N'-(2-hydroxycyclohexyl)oxamide is dissolved in a suitable organic solvent mixture, such as THF and DCM, and treated with about 1.1 equivalents Dess-Martin periodinane in the presence of an excess of a suitable inorganic base such as NaHCO₃ at 0° C. After warming to ambient temperature, the product may be isolated utilizing standard techniques well known in the art, such as extraction and purification by chromatographic methods. More specifically, the reaction mixture is quenched with aqueous sodium thiosulfate and aqueous saturated NaHCO₃. The reaction mixture is extracted with a suitable organic solvent such as DCM, the combined organic extracts are dried over a suitable drying agent such as Na₂SO₄, filtered, and concentrated to dryness. The crude product is subjected to purification over silica using a suitable organic solvent mixture, such as hexanes/EtOAc, to provide the product of Scheme 1, step B, N-allyl-N'-(2-oxocyclohexyl) oxamide.

In Scheme 1, step C, about 1 equivalent of N-allyl-N'-(2-oxocyclohexyl)oxamide, the product of Scheme 1, step B, is cyclized under thermal dehydrative conditions in the presence of a mixture of about 1.1 equivalents TFA and 1.1 equivalents trifluoroacetic anhydride in a suitable acidic solvent such as glacial acetic acid. The product may be isolated utilizing standard techniques well known in the art, such as evaporation and purification by chromatographic methods. More specifically, the reaction mixture is cooled to ambient temperature and evaporated under reduced pressure. The crude product is subjected to purification over silica using a suitable organic solvent mixture, such as MeOH/EtOAc, to provide the product of Scheme 1, step C, 4-allyl-5,6,7,8-tetrahydro-1H-quinoxaline-2,3-dione.

In Scheme 1, step D, about 1 equivalent of the product of Scheme 1, step C, 4-allyl-5,6,7,8-tetrahydro-1H-quinoxaline-2,3-dione, is treated with a suitable chlorinating agent, such as POCl₃, and subjected to heating in a suitable organic solvent, such as DCE. The reaction mixture is concentrated under reduced pressure after cooling to ambient temperature to provide the product of Scheme 1, step D, 1-allyl-3-chloro-3,4,5,6,7,8-hexahydroquinoxalin-2-one, suitable for subsequent use without further purification.

In scheme 1, step E, about 1 equivalent of 1-allyl-3-chloro-3,4,5,6,7,8-hexahydroquinoxalin-2-one, the product of Scheme 1, step D, is heated with about 5 equivalents of hydrazine in an appropriate polar organic solvent such as EtOH. The product may be isolated utilizing standard techniques well known in the art, such as extraction. More specifically, the reaction mixture is cooled and concentrated under reduced pressure, partitioned between water and an appropriate organic solvent, such as DCM, and the phases are separated. The organic extract is dried over Na₂SO₄, filtered, and concentrated under reduced pressure to obtain 1-allyl-3-hydrazino-5,6,7,8-tetrahydroquinoxalin-2-one, the product of Scheme 1, step E, suitable for subsequent use without additional purification.

In Scheme 1, step F, the product of Scheme 1, step E may be coupled to an acid using a variety of amide coupling techniques well known in the art. For example, about 1 equivalent of 1-allyl-3-hydrazino-5,6,7,8-tetrahydroquinoxalin-2-one, the product of step E, is dissolved in a suitable organic solvent, such as DMF, and treated with about 1.7 equivalents of a suitable amide coupling reagent, such as HATU or TBTU, and 1.7 equivalents of an appropriate carboxylic acid, such as 1-cyclopropylcyclopropanecarboxylic acid (see *Eur. J. Org Chem.*, 2010, pp 3295-3301), in the presence of 3.5-5 equivalents of a suitable non-nucleophilic organic base such as TEA or DIPEA. The product may be isolated utilizing standard techniques well known in the art, such as extraction. More specifically, the reaction mixture is diluted with EtOAc, washed sequentially with saturated aqueous NaHCO₃, and saturated aqueous NaCl, dried over Na₂SO₄, filtered, and concentrated under reduced pressure to obtain N'-(4-allyl-3-oxo-5,6,7,8-tetrahydroquinoxalin-2-yl)-1-cyclopropyl-cyclopropanecarbohydrazide, the product of Scheme 1, step F, which may be carried forward for use in the next step without additional purification.

In Scheme 1, step G, N'-(4-allyl-3-oxo-5,6,7,8-tetrahydroquinoxalin-2-yl)-1-cyclopropyl-cyclopropanecarbohydrazide, the product of Scheme 1, step F, may be cyclized under thermal or microwave conditions well known in the art. For example, N'-(4-allyl-3-oxo-5,6,7,8-tetrahydroquinoxalin-2-yl)-1-cyclopropyl-cyclopropanecarbohydrazide is dissolved in a suitable organic acid, such as AcOH, and heated in a microwave reactor. The product may be isolated utilizing standard techniques well known in the art, such as chromatographic methods. More specifically, the reaction mixture is concentrated under reduced pressure and the crude product is subjected to chromatography over silica, using an appropriate organic solvent mixture such as hexanes/EtOAc, to obtain 5-allyl-1-(1-cyclopropylcyclopropyl)-6,7,8,9-tetrahydro-[1,2,4]triazolo[4,3-a]quinoxalin-4-one, the product of Scheme 1, step G.

In Scheme 1, step H, 5-allyl-1-(1-cyclopropylcyclopropyl)-6,7,8,9-tetrahydro-[1,2,4]triazolo[4,3-a]quinoxalin-4-one, the product of Scheme 1, step G, may be deallylated under a variety of conditions well known in the art. For example, about 1 equivalent 5-allyl-1-(1-cyclopropylcyclopropyl)-6,7,8,9-tetrahydro-[1,2,4]triazolo[4,3-a]quinoxalin-4-one is dissolved in a suitable degassed organic solvent such as DCM. The solution is treated with about 3 equivalents N,N-dimethylbarbituric acid and about 0.2 equivalents tetrakis(triphenylphosphine)palladium with heating. The product may be isolated utilizing standard techniques well known in the art, such as chromatographic methods. More specifically, the reaction mixture is concentrated under reduced pressure and the resulting residue is subjected to reverse phase column chromatography, using a suitable mixture of buffered water and organic mobile phases, such as ACN containing about 0.1% TFA and water containing about 0.1% TFA, to obtain 1-(1-cyclopropylcyclopropyl)-6,7,8,9-tetrahydro-5H-[1,2,4]triazolo[4,3-a]quinoxalin-4-one, the product of Scheme 1, step H.

In Scheme 1, step I, the product of Scheme 1, step H may be alkylated under a variety of standard alkylation conditions well known in the art. For example, about 1 equivalent of 1-(1-cyclopropylcyclopropyl)-6,7,8,9-tetrahydro-5H-[1,2,4]triazolo[4,3-a]quinoxalin-4-one, the product of step H, is dissolved in a suitable organic solvent, such as DMF, and treated with about 3 equivalents of a suitable strong organic base, such as LHMDS, at or below ambient temperature. The subsequent reaction mixture is treated with a mixture of about 1 equivalent of an appropriate alkylating agent, such as bromomethylcyclopropane, and a catalytic amount of a halogen-transfer agent, such as KI. The product may be isolated utilizing standard techniques well known in the art, such as dilution followed by chromatographic methods. More specifically, the reaction mixture is diluted with an appropriate organic solvent such as EtOAc, washed with saturated aqueous NaCl, dried over $Na_2SO_4$, filtered, and concentrated under reduced pressure. The crude product is purified by chromatography over silica, using an appropriate polar organic solvent such as EtOAc, to obtain the compound of Formula I, 1-(1-cyclopropylcyclopropyl)-5-(cyclopropylmethyl)-6,7,8,9-tetrahydro-[1,2,4]triazolo[4,3-a]quinoxalin-4-one, the product of Scheme 1, step I.

washed sequentially with saturated $NaHCO_3$ followed by saturated aqueous NaCl, dried over $Na_2SO_4$, filtered, and concentrated under reduced pressure to obtain ethyl 2-(cyclopropylmethylamino)-2-oxo-acetate, the product of Scheme 2, step A, suitable for subsequent use without additional purification.

In Scheme 2, step B, amidation of ethyl 2-(cyclopropylmethylamino)-2-oxo-acetate may be performed under various conditions well known in the art. For example, about 1 equivalent ethyl 2-(cyclopropylmethylamino)-2-oxo-acetate, product of Scheme 2, step A, is dissolved in an appropriate organic solvent, such as DCM, and treated sequentially with about 1 equivalent of aminocyclohexanol and about 1 equivalent of a suitable non-nucleophilic

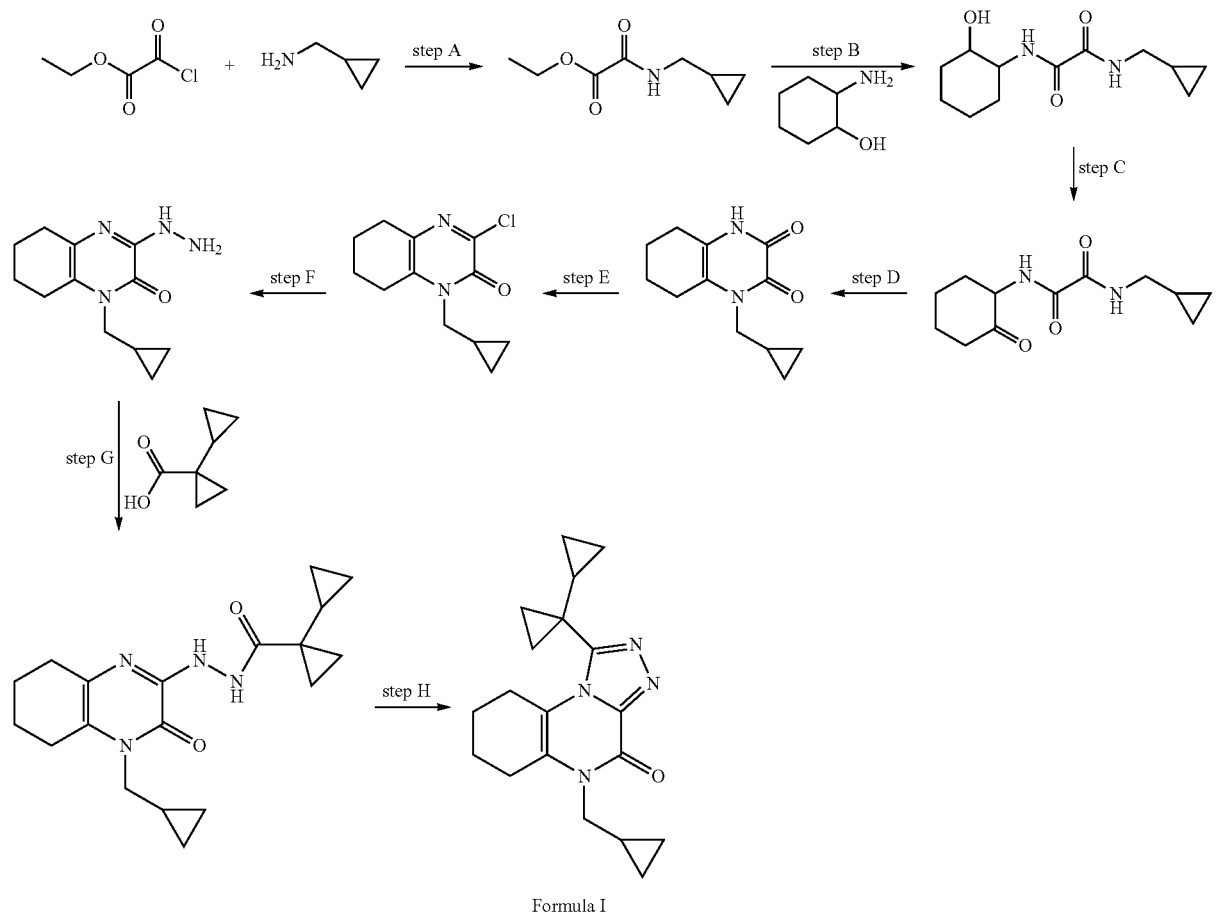

Formula I

Scheme 2 depicts an alternative synthesis to the compound of Formula I. In Scheme 2, step A, about 1 equivalent cyclopropylmethanamine in a typical organic solvent such as DCM is acylated with about 1 equivalent ethyl 2-chloro-2-oxo-acetate in the presence of about 1.1 equivalents of a non-nucleophilic organic base such as trimethylamine at about −20 to 0° C. The product may be isolated utilizing standard techniques well known in the art, such as extraction. More specifically, the reaction mixture is poured into water, the pH is adjusted to ~6-7 with an appropriate aqueous mineral acid such as 1 M HCl, and the acidified aqueous mixture is extracted with an appropriate organic solvent such as DCM. The combined organic extracts are organic base, such as TEA. After stirring at ambient temperature for 16-24 hr, the product may be isolated utilizing techniques well known in the art, such as filtration. For example, the resulting precipitate in the reaction mixture is collected by filtration, washed with a minimal amount of DCM, and air-dried to obtain N-(cyclopropylmethyl)-N'-(2-hydroxycyclohexyl)oxamide, the product of Scheme 2, step B, as a mixture of cis and trans isomers of sufficient purity for subsequent use without additional purification.

In Scheme 2, step C, N-(cyclopropylmethyl)-N'-(2-hydroxycyclohexyl)oxamide, the product of Scheme 2, step B, may be oxidized by conditions well known in the art. For example, about 1 equivalent N-(cyclopropylmethyl)-N'-(2- hydroxycyclohexyl) oxamide is dissolved in a suitable organic solvent such as DCM, cooled to 0° C., and slowly treated with about 2.5 equivalents of sulfur trioxide-pyridine complex. After warming to ambient temperature, the product may be isolated utilizing techniques well known in the art, such as extraction. For example, the reaction mixture is poured into water, neutralized to pH~7 with a suitable aqueous mineral acid such as 1 M aqueous HCl, and extracted with DCM. The combined organic extracts are washed sequentially with $H_2O$ followed by saturated aqueous NaCl, dried over $Na_2SO_4$, filtered, and concentrated under reduced pressure to obtain N-(cyclopropylmethyl)-N'-(2-oxocyclohexyl)oxamide, the product of Scheme 2, step C, suitable for subsequent use without additional purification.

In Scheme 2, step D, cyclization of N-(cyclopropylmethyl)-N'-(2-oxocyclohexyl)oxamide, the product of Scheme 2, step C, may be performed in a manner similar to that described in Scheme 1, step C to obtain 4-(cyclopropylmethyl)-5,6,7,8-tetrahydro-1H-quinoxaline-2,3-dione, the product of Scheme 2 step D.

In Scheme 2, step E, chlorination of 4-(cyclopropylmethyl)-5,6,7,8-tetrahydro-1H-quinoxaline-2,3-dione, the product if Scheme 2, step D, may be performed as described in Scheme 1, step D, to obtain 3-chloro-1-(cyclopropylmethyl)-5,6,7,8-tetrahydroquinoxalin-2-one, the product of Scheme 2, step E.

In Scheme 2, step F, 3-chloro-1-(cyclopropylmethyl)-5,6,7,8-tetrahydroquinoxalin-2-one, the product of Scheme 2, step E, may be treated with hydrazine under conditions similarly described in Scheme 1, step E, to obtain 1-(cyclopropylmethyl)-3-hydrazino-5,6,7,8-tetrahydroquinoxalin-2-one, the product of Scheme 2, step F.

In Scheme 2, step G, 1-(cyclopropylmethyl)-3-hydrazino-5,6,7,8-tetrahydroquinoxalin-2-one, the product of Scheme 2, step F, may be coupled to an acid using a variety of amide coupling techniques well known in the art. For example, about 1 equivalent of 1-(cyclopropylmethyl)-3-hydrazino-5,6,7,8-tetrahydroquinoxalin-2-one is dissolved in a suitable organic solvent such as DMF and treated sequentially with about 1.5 equivalents of 1-cyclopropylcyclopropane-carboxylic acid (see Eur. J. Org Chem., 2010, pp 3295-3301), 1.6 equivalents EDCI, about 1.7 equivalents HOAT, and about 3 equivalents of a suitable non-nucleophilic organic base such as TEA. After stirring for about 16 hr at ambient temperature, the product may be isolated utilizing techniques well known in the art, such as extraction. For example, the reaction mixture is partitioned between $H_2O$ and MTBE, the phases separated, and the aqueous phase is acidified with an appropriate aqueous mineral acid such as 0.5 M HCl. The acidified aqueous solution is extracted with an appropriate organic solvent such as DCM, the layers separated, and the organic layer dried over $Na_2SO_4$, filtered, and concentrated under reduced pressure to obtain 1-cyclopropyl-N'-[4-(cyclopropylmethyl)-3-oxo-5,6,7,8-tetrahydroquinoxalin-2-yl]cyclopropanecarbohydrazide, the product of Scheme 2, step G, suitable for subsequent use without additional purification.

In Scheme 2, step H, about 1 equivalent of 1-cyclopropyl-N'-[4-(cyclopropylmethyl)-3-oxo-5,6,7,8-tetrahydroquinoxalin-2-yl]cyclopropanecarbo-hydrazide, the product of Scheme 2, step G, is cyclized under thermal conditions in an organic solvent such as HMDS containing 0.2 equivalents of a suitable non-nucleophilic organic base such as DBU. After heating for about 16 hr, the product may be isolated by utilizing techniques well known in the art, such as filtration, extraction, and trituration. For example, the cooled reaction mixture is filtered, and the collected solids are dissolved in a suitable organic solvent such as DCM. The organic solution is washed with saturated aqueous NaCl, dried over $Na_2SO_4$, filtered and concentrated under reduced pressure. The crude product is triturated with a minimal amount of ACN and the solid collected by filtration, redissolved in a minimal amount of EtOAc, and concentrated under reduced pressure to obtain 1-(1-cyclopropylcyclopropyl)-5-(cyclopropylmethyl)-6,7,8,9-tetrahydro-[1,2,4]triazolo[4,3-a]quinoxalin-4-one, the product of Scheme 2, step H, of sufficient purity without additional purification.

Preparation 1

N-allyl-N'-(2-hydroxycyclohexyl)oxamide

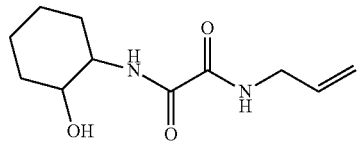 [SMILES: C=CCNC(=O)C(=O)NC1CCCCC1O]

Scheme 1, step A: Combine 2-aminocyclohexanol (7.7 g, 66.8 mmol), ethyl-2-(allylamino)-2-oxo-acetate (10.0 g, 63.6 mmol) and triethylamine (9.8 mL, 70.0 mmol) in EtOAc (127.3 mL) and heat the mixture at 80° C. for 4 hr. Cool the mixture to ambient temperature and stir overnight. Isolate the resulting precipitate by vacuum filtration, wash the filter cake with EtOAc, and dry for 4 hr to give the title compound (7.2 g, 50%) as a white, crystalline solid. Concentrate the filtrate under reduced pressure and sonicate the resulting solid in $Et_2O$. Isolate the solid by vacuum filtration, wash the filter cake with $Et_2O$, and dry for 1.5 hr to give an additional lot of the title compound (2.8 g, 19%) as a white, crystalline solid. The product is a mixture of cis and trans isomers. LC-ES/MS (m/z): 227.0 (M+H).

Preparation 2

N-allyl-N'-(2-oxocyclohexyl)oxamide

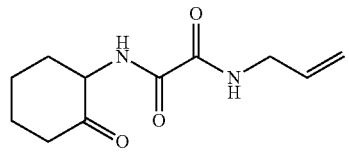 [SMILES: C=CCNC(=O)C(=O)NC1CCCCC1=O]

Scheme 1, step B: Combine N'-allyl-N-(2-hydroxycyclohexyl)oxamide (5.0 g, 22.1 mmol) and $NaHCO_3$ (25.0 g, 297.6 mmol) in a mixture of DCM (110.5 mL) and THF (36.8 mL) and chill the resulting suspension to 0° C. Add 3,3,3-triacetoxy-3-iodophthalide (10.3 g, 24.3 mmol) to the suspension and allow the mixture to slowly warm to ambient temperature. After stirring overnight at ambient temperature, quench the mixture by the addition of saturated $Na_2S_2O_3$ (7.0 g in 50 mL of $H_2O$) and saturated $NaHCO_3$. Stir the biphasic mixture at ambient temperature for 2 hr and separate the layers. Extract the aqueous layer with DCM. Combine the organic extracts, dry over Na$_2$SO$_4$, filter, and concentrate under reduced pressure to give a residue. Purify the residue by flash chromatography over silica, eluting with EtOAc:hexanes (1:1), to give the title compound (3.4 g, 69%) as an off-white solid. LC-ES/MS (m/z): 225.0 (M+H).

Preparation 3

4-allyl-5,6,7,8-tetrahydro-1H-quinoxaline-2,3-dione

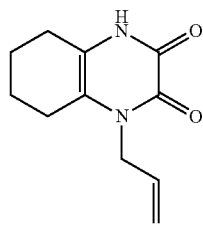

Scheme 1, step C: Add N-allyl-N'-(2-oxocyclohexyl)oxamide (3.4 g, 15.2 mmol) to a mixture of AcOH (15.2 mL, 264.6 mmol), TFA (1.3 mL, 16.7 mmol), and TFAA (3.5 g, 16.7 mmol) and heat the mixture at 100° C. overnight. Cool the mixture to ambient temperature and remove the solvent under reduced pressure to give a black oil. Purify the residue by flash chromatography over silica, eluting with MeOH:EtOAc (gradient of 0:1 to 1:4), to give the title compound (2.6 g, 83%) as a tan solid. LC-ES/MS (m/z): 207.0 (M+H).

Preparation 4

1-allyl-3-chloro-3,4,5,6,7,8-tetrahydroquinoxalin-2-one

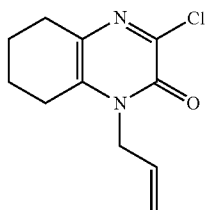

Scheme 1, step D: Add POCl$_3$ (2.0 g, 13.1 mmol) to a solution of 4-allyl-5,6,7,8-tetrahydro-1H-quinoxaline-2,3-dione (2.6 g, 12.5 mmol) dissolved in DCE (62.6 mL) and heat the mixture at 75° C. for 4.5 hr. Add additional POCl$_3$ (1.0 g, 6.3 mmol) to the mixture and continue heating at 75° C. for 3.5 hr. Cool the mixture to ambient temperature and stir overnight. Remove the solvent under reduced pressure and dissolve the resulting residue in toluene. Remove the toluene under reduced pressure to give the title compound (2.81 g, 100%) as a dark red oil. LC-ES/MS (m/z): 225.0 (M+H).

Preparation 5

1-allyl-3-hydrazino-5,6,7,8-tetrahydroquinoxalin-2-one

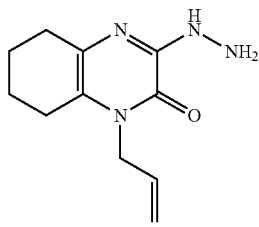 [SMILES: C=CCn1c2c(nc(NN)c1=O)CCCC2]

Scheme 1, step E: Add hydrazine (2.0 g, 62.5 mmol) to a suspension of 1-allyl-3-chloro-3,4,5,6,7,8-hexahydroquinoxalin-2-one (2.8 g, 12.5 mmol) in EtOH (50 mL) and heat the mixture overnight at reflux. Cool the mixture to ambient temperature and remove the solvent under reduced pressure. Partition the resulting residue between H$_2$O and DCM. Separate the organic layer and extract the aqueous with DCM. Combine the organic extracts, dry over Na$_2$SO$_4$, filter, and concentrate under reduced pressure to give the title compound (2.6 g, 95%) as an orange oil. LC-ES/MS (m/z): 221.0 (M+H).

Preparation 6

N'-(4-allyl-3-oxo-5,6,7,8-tetrahydroquinoxalin-2-yl)-1-cyclopropyl-cyclopropanecarbohydrazide

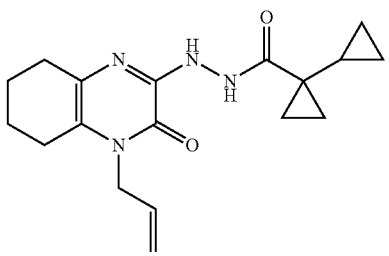 [SMILES: C=CCn1c2c(nc(NNC(=O)C3(C4CC4)CC3)c1=O)CCCC2]

Scheme 1, step F: Add 1-cyclopropylcyclopropanecarboxylic acid (2.3 g, 18.3 mmol, see *Eur. J. Org Chem.*, 2010, pp 3295-3301), HATU (7.0 g, 18.3 mmol), and DIPEA (6.6 mL, 37.7 mmol) to a solution of 1-allyl-3-hydrazino-5,6,7,8-tetrahydroquinoxalin-2-one (2.4 g, 10.8 mmol) in DMF (40 mL) and stir the mixture overnight at ambient temperature. Dilute the mixture with EtOAc and wash the mixture sequentially with saturated NaHCO$_3$ and saturated aqueous NaCl. Dry the organic mixture over Na$_2$SO$_4$, filter, and concentrate under reduced pressure to give the title compound (3.5 g, 100%) as a brown oil. LC-ES/MS (m/z): 329.2 (M+H).

Preparation 7

5-allyl-1-(1-cyclopropylcyclopropyl)-6,7,8,9-tetrahydro-[1,2,4]triazolo[4,3-a]quinoxalin-4-one

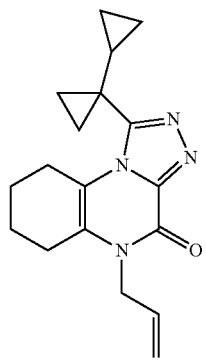 [SMILES: C=CCn1c2c(n3c(C4(C5CC5)CC4)nnc3c1=O)CCCC2]

Scheme 1, step G: Dissolve N'-(4-allyl-3-oxo-5,6,7,8-tetrahydroquinoxalin-2-yl)-1-cyclopropyl-cyclopropanecarbohydrazide (3.5 g, 10.8 mmol) in AcOH (10.0 mL, 174.5 mmol) and heat the solution in a microwave at 130° C. for 3.5 hr. Remove the AcOH under reduced pressure and purify the resulting residue by flash chromatography over silica, eluting with EtOAc:hexanes (gradient of 4:1 to 1:0), to give the title compound (1.2 g, 35%) as a brown oil. LC-ES/MS (m/z): 311.2 (M+H).

Preparation 8

1-(1-cyclopropylcyclopropyl)-6,7,8,9-tetrahydro-5H-[1,2,4]triazolo[4,3-a]quinoxalin-4-one

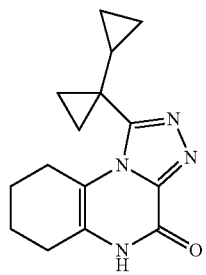 [SMILES: O=c1[nH]c2c(n3c(C4(C5CC5)CC4)nnc13)CCCC2]

Scheme 1, step H: Add N,N-dimethylbarbituric acid (1.3 g, 8.5 mmol) to a solution of 5-allyl-1-(1-cyclopropylcyclopropyl)-6,7,8,9-tetrahydro-[1,2,4]triazolo[4,3-a]quinoxalin-4-one (877.4 mg, 2.8 mmol) in DCM (30 mL) and purge with nitrogen for 10 minutes. Add tetrakis(triphenylphosphine)palladium (653.3 mg, 565.3 µmol) and heat the mixture at 35° C. overnight. Cool the mixture to ambient temperature and remove the solvent under reduced pressure to give a residue. Purify the residue by reverse phase flash chromatography (REDISEP™ Gold C-18, 415 g; gradient: 20-48% of a mixture of 0.1% TFA in ACN in a mixture of 0.1% TFA in H₂O over 22.9 min.) to give the title compound (392.7 mg, 51%) as a tan solid. LC-ES/MS (m/z): 271.0 (M+H).

Preparation 9 ethyl 2-(cyclopropylmethylamino)-2-oxo-acetate

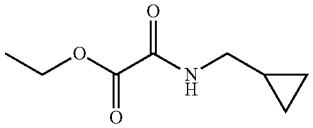

Scheme 2, step A: Add TMA (90 g, 0.9 mol) to a −10° C. solution of ethyl 2-chloro-2-oxo-acetate (109 g, 0.8 mol) in DCM (1.5 L). Add cyclopropylmethanamine (60 g, 0.8 mol) to the solution drop wise over 20 minutes at −10° C. and stir the mixture for 3 hr at −10° C. Pour the mixture into H₂O (1.5 L) and adjust to pH~5-6 with 1M HCl. Separate the layers and wash the organic layer sequentially with saturated NaHCO₃ (500 mL) and saturated aqueous NaCl (500 mL). Dry the organic layer over Na₂SO₄ and concentrate under reduced pressure to give the title compound (129 g, 94%) as a yellow oil. LC-ES/MS (m/z): 172.2 (M+H).

Preparation 10

N-(cyclopropylmethyl)-N'-(2-hydroxycyclohexyl)oxamide

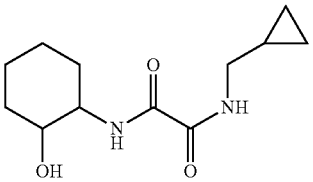 [SMILES: O=C(NCC1CC1)C(=O)NC1CCCCC1O]

Scheme 2, step B: Add TEA (115 mL, 0.8 mol) to a solution of ethyl 2-(cyclopropylmethylamino)-2-oxo-acetate (128.5 g, 0.75 mol) in DCM (1.6 L) at ambient temperature. Add 2-aminocyclohexanol (91 g, 0.8 mol) to the mixture and stir for 16 hr at ambient temperature. Filter the resulting precipitate and air dry to give the title compound (147 g, 80%) as a white solid mixture of cis and trans isomers. LC-ES/MS (m/z) 241.1 (M+H).

Preparation 11

N-(cyclopropylmethyl)-N'-(2-oxocyclohexyl)oxamide

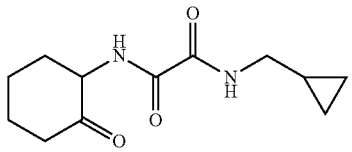 [SMILES: O=C(NCC1CC1)C(=O)NC1CCCCC1=O]

Scheme 2, step C: Add TEA (320 mL, 2.3 mol) over 1 hr to a slurry of N-(cyclopropylmethyl)-N'-(2-hydroxycyclohexyl)oxamide (137 g, 0.6 mol) in DCM (1.4 L) at 0° C. Dissolve sulfur trioxide-pyridine complex (365 g, 2.3 mol)

in DMSO (730 mL) and add the solution drop wise to the reaction mixture at 0° C. Allow the mixture to warm to ambient temperature and stir for 16 hr. Pour the reaction mixture into H$_2$O (800 mL) and adjust to pH~7 using 1M HCl. Separate the layers and wash the organic layer sequentially with H$_2$O (300 mL) and saturated aqueous NaCl (200 mL). Dry the organic extract over Na$_2$SO$_4$ and concentrate under reduced pressure to give the title compound (114 g, 83%) as a white solid. LC-ES/MS (m/z) 239.1 (M+H).

Preparation 12

4-(cyclopropylmethyl)-5,6,7,8-tetrahydro-1H-quinoxaline-2,3-dione

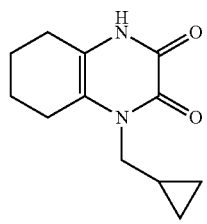 [SMILES: O=c1[nH]c2c(n(CC3CC3)c1=O)CCCC2]

Scheme 2, step D: Add TFA (60 g, 0.5 mol) and TFAA (111 g, 0.5 mol) to a solution of N-(cyclopropylmethyl)-N'-(2-oxocyclohexyl)oxamide (114 g, 0.5 mol) in AcOH (574 mL) and heat the mixture at 100° C. for 18 hr. Remove the AcOH under reduced pressure and add H$_2$O (500 mL) and DCM (400 mL) to the resulting residue. Adjust the pH to ~7 using aqueous NaHCO$_3$ and separate the layers. Wash the organic layer sequentially with H$_2$O (200 mL) and saturated aqueous NaCl (200 mL). Dry the organic extract over Na$_2$SO$_4$ and concentrate under reduced pressure to give the crude product as a solid. Triturate the solid with ACN (3 mL/g) and isolate by vacuum filtration to give the title compound (42 g, 38%) as a white solid. LC-ES/MS (m/z) 221.1 (M+H).

Preparation 13

3-chloro-1-(cyclopropylmethyl)-5,6,7,8-tetrahydroquinoxalin-2-one

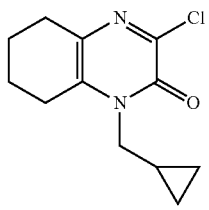 [SMILES: O=c1c(Cl)nc2c(n1CC1CC1)CCCC2]

Scheme 2, step E: Combine 4-(cyclopropylmethyl)-5,6,7,8-tetrahydro-1H-quinoxaline-2,3-dione (41.5 g, 0.19 mol) and POCl$_3$ (37.7 g, 0.3 mol) in DCE (415 mL) and heat the mixture at 75° C. for 5 hr. Cool the mixture to ambient temperature and pour into saturated KH$_2$PO$_4$ solution (1 L). Separate the layers and wash the organic layer sequentially with H$_2$O (300 mL) and saturated aqueous NaCl (300 mL). Dry the organic extract over Na$_2$SO$_4$ and concentrate under reduced pressure to give the title compound (38.3 g, 85%) as a brown solid. LC-ES/MS (m/z): 239.1 (M+H).

Preparation 14

1-(cyclopropylmethyl)-3-hydrazino-5,6,7,8-tetrahydroquinoxalin-2-one

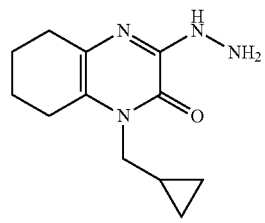 [SMILES: NNc1nc2c(n(CC3CC3)c1=O)CCCC2]

Scheme 2, step F: Add hydrazine (80.6 g, 1.6 mol) to a solution of 3-chloro-1-(cyclopropylmethyl)-5,6,7,8-tetrahydroquinoxalin-2-one (38.3 g, 0.16 mol) in EtOH (153 mL) and heat the mixture at 75° C. for 4 hr. Cool the mixture to ambient temperature and pour into H$_2$O (300 mL). Isolate the resulting yellow precipitate by vacuum filtration. Dissolve the filter cake in DCM (200 mL). Dry the organic solution over Na$_2$SO$_4$ and concentrate under reduced pressure to give the title compound (28.7 g, 76%) as an off-white solid. LC-ES/MS (m/z): 235.2 (M+H).

Preparation 15

1-cyclopropyl-N'-[4-(cyclopropylmethyl)-3-oxo-5,6,7,8-tetrahydroquinoxalin-2-yl]cyclopropanecarbohydrazide

SP-0010427-181-A

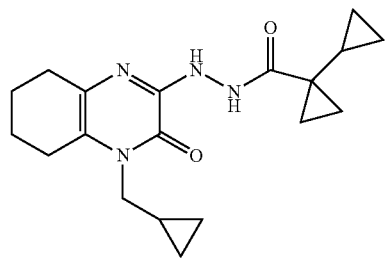 [SMILES: O=C(NNc1nc2c(n(CC3CC3)c1=O)CCCC2)C1(C2CC2)CC1]

Scheme 2, step G: Add EDCI (36.4 g, 0.19 mol), HOAT (26.9 g, 0.2 mol), TEA (38.5 g, 0.4 mol), and 1-(cyclopropylmethyl)-3-hydrazino-5,6,7,8-tetrahydroquinoxalin-2-one (28.7 g, 0.12 mol) to a solution of 1-cyclopropylcyclopropanecarboxylic acid (23.2 g, 0.18 mol, see *Eur. J. Org Chem.*, 2010, pp 3295-3301) in DMF (430 mL) at 0° C. Warm the reaction mixture to ambient temperature, stir for 16 hr, and then pour into a mixture of H$_2$O (800 mL) and MTBE (700 mL). Separate the layers and extract the organic layer with 0.5M HCl (300 mL). Discard the organic layer and adjust the aqueous layer to pH~8 with saturated NaHCO$_3$. Extract the aqueous layer with DCM, separate the layers, and concentrate the organic extract under reduced pressure to give the title compound (38 g, 91%) as an off-white solid. LC-ES/MS (m/z): 343.2 (M+H).

EXAMPLE 1

1-(1-cyclopropylcyclopropyl)-5-(cyclopropylmethyl)-6,7,8,9-tetrahydro-[1,2,4]triazolo[4,3-a]quinoxalin-4-one

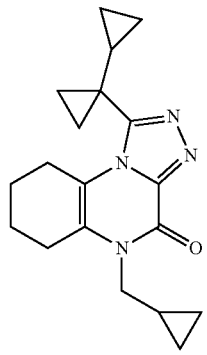 [SMILES: O=c1c2nnc(C3(C4CC4)CC3)n2c2c(n1CC1CC1)CCCC2]

Scheme 1, step I: Add LHMDS (1.6 g, 1.8 mmol) to a solution of 1-(1-cyclopropylcyclopropyl)-6,7,8,9-tetrahydro-5H-[1,2,4]triazolo[4,3-a]quinoxalin-4-one (164.2 mg, 607.4 μmol) in DMF (5 mL). After stirring the mixture for 1 hour at ambient temperature, add KI (10 mg, 60.7 μmol) and bromomethylcyclopropane (246.0 mg, 1.8 mmol) and stir the mixture at ambient temperature for 2 days. Dilute the mixture with EtOAc and wash with saturated aqueous NaCl. Dry over $Na_2SO_4$, filter, and concentrate under reduced pressure to give an oil. Purify by flash chromatography on silica, eluting with EtOAc (100%), to give the title compound (108.2 mg, 55%) as a tan solid. LC-ES/MS (m/z): 325.2 (M+H).

Alternative Procedure for Example 1

1-(1-cyclopropylcyclopropyl)-5-(cyclopropylmethyl)-6,7,8,9-tetrahydro-[1,2,4]triazolo[4,3-a]quinoxalin-4-one

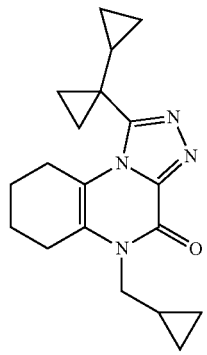 [SMILES: O=c1c2nnc(C3(C4CC4)CC3)n2c2c(n1CC1CC1)CCCC2]

Scheme 2, step H: Combine 1-cyclopropyl-N'-[4-(cyclopropylmethyl)-3-oxo-5,6,7,8-tetrahydroquinoxalin-2-yl]cyclopropanecarbohydrazide (35.7 g, 0.1 mol), HMDS (357 mL), and DBU (2.9 g, 0.02 mol) and heat the mixture at 125° C. for 16 hr. Cool the mixture to ambient temperature and pour into $H_2O$ (260 mL). Collect the precipitate by vacuum filtration and dissolve the solid in DCM (200 mL). Wash the organic solution with saturated aqueous NaCl, separate the layers, dry the organic layer over $Na_2SO_4$, and concentrate under reduced pressure to give a solid. Triturate the solid with ACN (2 mL/g) and collect by vacuum filtration. Dissolve the collected solid in EtOAc and concentrate under reduced pressure to give the title compound (20 g, 59%) as a pale yellow solid. LC-ES/MS (m/z): 325.2 (M+H).

Generation of PDE Proteins

The nucleotide sequences encoding full-length human $PDE_1A$ (NP_001003683.1), PDE1C (NP_005011.1), PDE5A (NP_001074.2), PDE7B (NP_061818.1) and PDE9A (NP_002597.1) are inserted into pFastBac1 (Invitrogen) vector with an N-terminal HIS tag. The nucleotide sequences encoding full-length human PDE4D (NP_006194.2) and catalytic domain (residue 641-1141) of PDE3A (NP_000912.3) are inserted into pFastBac1 (Invitrogen) vector with a C-terminal HIS tag. The nucleotide sequences encoding full-length human PDE8A (NP_002596.1) and PDE11A (AAI12394.1) are inserted into pFastBac1 (Invitrogen) vector with an N-terminal Flag tag. The nucleotide sequences encoding full-length human PDE10A (AAD32595.1) are inserted into pFastBac1 (Invitrogen) vector with a C-terminal Flag-His tag. The nucleotide sequences encoding full-length human PDE6A (NP_000431.2) and PDE6B (AAH00249.1) are inserted into pFastBacDual (Invitrogen) vector with an N-terminal HIS tag and N-terminal Flag tag, respectively, for production of PDE6A/6B dimer. Baculovirus generation and protein expression in Sf9 cells are carried out according to the protocol of Bac-to-Bac Baculovirus Expression system (Invitrogen). The nucleotide sequences encoding full-length human PDE1B (NP_000915.1) and PDE2A (NP_002590.1) are inserted into pIEX4 (Novagen) with a C-terminal HIS tag, and both protein productions in Sf9 cells are carried out according to the vendor's protocol (Novagen). The His tagged PDE proteins are purified using Ni-NTA agarose (Qiagen) followed by size exclusion chromatography on a SUPERDEX® 200 column (GE Healthcare) in storage buffer (20 mM Tris-HCl, pH7.5, 150 mM NaCl, 10% Glycerol). The Flag tagged PDE proteins including PDE6A/6B are purified using anti-Flag M2-agarose (Sigma), after purification through NiNTA column chromatography and eluted in storage buffer (50 mM Tris-HCl, pH7.5, 150 mM NaCl, 10% Glycerol, 0.1 mg/ml Flag peptide). All purified proteins are stored at −80° C. in small aliquots.

Phosphodiesterase Enzyme Assays

All 3', 5' cyclic nucleotide phosphodiesterase (PDE) enzyme activities are measured with a radiometric enzyme assay based on SPA detection system (scintillation proximity assay). Compounds to be tested are diluted in pure dimethyl sulfoxide (DMSO) using ten point concentration response curves. Maximal compound concentration in the reaction mixture is either 10 or 100 μM. Compounds at the appropriate concentration are pre-incubated with either of the PDE enzymes for 30 minutes before the reaction is started by the addition of substrate. Reactions are allowed to proceed for 60 minutes at room temperature. Next, reactions are stopped by addition of SPA beads. Samples are read 12 hours later in a MICROBETA™ TRILUX® Counter. "$IC_{50}$" refers to the concentration of the compound that produces 50% of the maximal inhibitory response possible for that compound. $IC_{50}$ values are calculated by plotting the normalized data vs. log [compound] and fitting the data using a four parameter logistic equation.

Ca$^{2+}$—Calmodulin Dependent PDE Enzyme Assays

PDE1B, PDE1A, and PDE1C are cloned and purified in house following standard protein generation procedures. The assay buffer is prepared to give a final concentration in the assay of 50 mM Tris-HCl, 50 mM MgCl$_2$, 4 mM CaCl$_2$, 0.1% Bovine serum albumin and 6 U/ml Calmodulin in water, at pH 7.5. The final enzyme concentration is 0.25, 0.074 and 0.0012 nM, for PDE1A, PDE1B and PDE1C respectively. The reactions are started by addition of the substrate, [$^3$H]cAMP, to give a final concentration of 47 nM.

TABLE 1

In vitro potency of Example 1 against PDE1A, PDE1B, and PDE1C.

| PDE enzymes | IC$_{50}$ (nM) of Example 1 |
|---|---|
| PDE 1A | 3.41 |
| PDE 1B | 4.91 |
| PDE 1C | 3.05 |

The data in Table 1 demonstrate that the compound of Example 1 inhibits PDE1A, PDE1B, and PDE1C enzyme activity in vitro.

PDE Enzyme Assays Using [$^3$H]cAMP as Substrate

The following phosphodiesterase activities are measured using [$^3$H]cAMP as reaction substrate: PDE3A (catalytic domain), PDE4D, PDE7B and PDE8A. All these enzymes are cloned and purified in house following standard procedures. The assay buffer is prepared to give a final concentration in the assay of 50 mM Tris-HCl, 8.3 mM MgCl$_2$, 1.7 mM ethylenediaminetetraacetic acid (EDTA) and 0.1% Bovine serum albumin at pH 7.5. Final enzyme concentrations are 0.008, 0.021, 0.5 and 0.06 nM for PDE3A, PDE4D, PDE7B and PDE8A respectively. Reactions are also started by addition of the substrate, [$^3$H]cAMP, to give a final concentration of 47 nM.

TABLE 2

In vitro potency of Example 1 against PDE3A (catalytic domain), PDE4D, PDE7B and PDE8A.

| PDE enzymes | IC$_{50}$ (nM) of Example 1 |
|---|---|
| PDE3A | >100000 |
| PDE4D | 7060 |
| PDE7B | 2180 |
| PDE8A | >10000 |

PDE Enzyme Assays Using [$^3$H]cGMP as Substrate

The following phosphodiesterase activities are measured using [$^3$H]cGMP as reaction substrate: PDE2A, PDE5A, PDE6A/6B, PDE9A, PDE10A and PDE11A. The catalytic active form of PDE6 is a dimer composed of a α (PDE6A) and β subunits (PDE6B). The dimer of PDE6A/6B is produced by the expression and purification strategy, using two purification steps, i.e., NiNTA and anti-FLAG Sepharose chromatography. The rest of the enzymes are cloned and purified in house following standard procedures. The assay buffer is prepared to give a final concentration in the assay of 50 mM Tris-HCl, 8.3 mM MgCl$_2$, 1.7 mM EDTA and 0.1% Bovine serum albumin at pH 7.5. Final enzyme concentrations are 0.2, 0.002, 5, 1, 0.03 and 0.03 nM for PDE2A, PDE5A, PDE6AB, PDE9A, PDE10A and PDE11A, respectively. The reactions are started by addition of the substrate, [$^3$H]cGMP, to give a final concentration of 80 nM in the case of PDE2A, PDE10A, PDE5A, PDE6AB and PDE11A assays, whereas for PDE9A 20 nM of [$^3$H] cGMP is used.

TABLE 3

In vitro potency of Example 1 against PDE2A, PDE5A, PDE6AB, PDE9A, PDE10A and PDE11A.

| PDE enzymes | IC$_{50}$ (nM) of Example 1 |
|---|---|
| PDE2A | >10000 |
| PDE5A | >10000 |
| PDE 6AB | >10000 |
| PDE9A | >10000 |
| PDE10A | >10000 |
| PDE11A | 2970 |

The data in Tables 2 and 3 demonstrate that the compound of Example 1 is a selective inhibitor of PDE1A, PDE1B, and PDE1C relative to PDE2A, PDE3A, PDE4D, PDE5A, PDE6AB, PDE7B, PDE8A, PDE9A, PDE10A, and PDE11A in vitro.

I claim:

1. A method of treating chronic kidney disease in a patient, comprising administering to a patient in need thereof an effective amount of a compound of the formula:

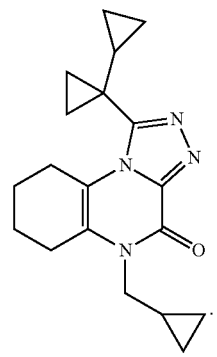 [SMILES: O=c1c2nnc(C3(C4CC4)CC3)n2c2c(n1CC1CC1)CCCC2]

2. A method of treating diabetic kidney disease in a patient, comprising administering to a patient in need thereof an effective amount of a compound of the formula:

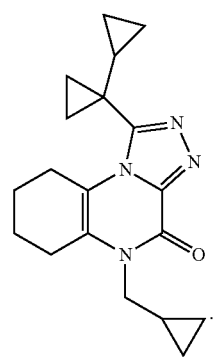 [SMILES: O=c1c2nnc(C3(C4CC4)CC3)n2c2c(n1CC1CC1)CCCC2]

* * * * *